(12) United States Patent
Youker

(10) Patent No.: US 7,917,207 B2
(45) Date of Patent: Mar. 29, 2011

(54) METHOD AND APPARATUS FOR AN IMPLANTABLE PULSE GENERATOR WITH A STACKED BATTERY AND CAPACITOR

(75) Inventor: Nick A. Youker, River Falls, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/178,876

(22) Filed: Jul. 24, 2008

(65) Prior Publication Data

US 2009/0025207 A1    Jan. 29, 2009

Related U.S. Application Data

(63) Continuation of application No. 11/117,952, filed on Apr. 29, 2005, now abandoned.

(51) Int. Cl.
*A61N 1/375* (2006.01)
(52) U.S. Cl. .............................................. 607/2
(58) Field of Classification Search .............. 607/36, 607/2, 37
See application file for complete search history.

(56) References Cited

U.S. PATENT DOCUMENTS

| | | | |
|---|---|---|---|
| 3,993,508 A | 11/1976 | Erlichman | |
| 4,113,921 A | 9/1978 | Goldstein et al. | |
| 4,243,042 A | 1/1981 | Ware | |
| 4,659,636 A | 4/1987 | Suzuki et al. | |
| 5,131,388 A | 7/1992 | Pless et al. | |
| 5,370,663 A | 12/1994 | Lin | |
| 5,370,669 A | 12/1994 | Daglow et al. | |
| 5,456,698 A | 10/1995 | Byland et al. | |
| 5,522,851 A | 6/1996 | Fayram | |
| 5,527,346 A | 6/1996 | Kroll | |
| 5,640,756 A | 6/1997 | Brown et al. | |
| 5,658,319 A | 8/1997 | Kroll | |

(Continued)

FOREIGN PATENT DOCUMENTS

WO    WO-2005070498 A1    8/2005

(Continued)

OTHER PUBLICATIONS

"U.S. Appl. No. 09/165,779, Amendment and Response filed Feb. 22, 2000 to Restriction Requirement mailed Jan. 19, 2000", 5 pages.

(Continued)

*Primary Examiner* — Scott M Getzow
*Assistant Examiner* — Amanda Patton
(74) *Attorney, Agent, or Firm* — Schwegman, Lundberg & Woessner, P.A.

(57) ABSTRACT

The present subject matter includes one embodiment of an apparatus, comprising: a battery including a plurality of flat battery layers disposed in a battery case, the battery case having a planar battery surface which has a battery perimeter; and a capacitor including a plurality of flat capacitor layers disposed in a capacitor case, the capacitor case having a planar capacitor surface which has a capacitor perimeter, the capacitor stacked with the battery such that the planar battery surface and the planar capacitor surface are adjacent, with the capacitor perimeter and the battery perimeter substantially coextensive; a hermetically sealed implantable housing having a first shell and a lid mated to the first shell at a first opening, the first opening sized for passage of the battery, the capacitor, and the programmable electronics, wherein the battery and the capacitor are disposed in the hermetically sealed implantable housing.

13 Claims, 4 Drawing Sheets

U.S. PATENT DOCUMENTS

| | | | |
|---|---|---|---|
| 5,691,079 A | 11/1997 | Daugaard | |
| 5,697,953 A | 12/1997 | Kroll et al. | |
| 5,749,911 A | 5/1998 | Westlund | |
| 5,776,632 A | 7/1998 | Honegger | |
| 5,800,857 A | 9/1998 | Ahmad et al. | |
| 5,801,917 A | 9/1998 | Elias | |
| 5,814,082 A | 9/1998 | Fayram et al. | |
| 5,882,362 A | 3/1999 | Muffoletto et al. | |
| 6,006,133 A | 12/1999 | Lessar et al. | |
| 6,009,348 A | 12/1999 | Rorvick et al. | |
| 6,010,317 A | 1/2000 | Maget et al. | |
| 6,032,075 A | 2/2000 | Pignato et al. | |
| 6,040,082 A | 3/2000 | Haas et al. | |
| 6,042,624 A | 3/2000 | Breyen et al. | |
| 6,118,651 A | 9/2000 | Mehrotra et al. | |
| 6,118,652 A | 9/2000 | Casby et al. | |
| 6,184,160 B1 | 2/2001 | Yan et al. | |
| 6,212,063 B1 | 4/2001 | Johnson et al. | |
| 6,275,729 B1 | 8/2001 | O'Phelan et al. | |
| 6,297,943 B1 | 10/2001 | Carson | |
| 6,330,925 B1 | 12/2001 | Ovshinsky et al. | |
| 6,371,997 B1 | 4/2002 | Chang et al. | |
| 6,388,284 B2 | 5/2002 | Rhodes et al. | |
| 6,388,866 B1 * | 5/2002 | Rorvick et al. | 361/503 |
| 6,404,619 B1 | 6/2002 | Marshall et al. | |
| 6,445,948 B1 | 9/2002 | Somdahl et al. | |
| 6,459,566 B1 | 10/2002 | Casby et al. | |
| 6,498,951 B1 | 12/2002 | Larson et al. | |
| 6,522,525 B1 | 2/2003 | O'Phelan et al. | |
| 6,556,863 B1 | 4/2003 | O'Phelan et al. | |
| 6,571,126 B1 | 5/2003 | O'Phelan et al. | |
| 6,674,634 B2 | 1/2004 | O'Phelan et al. | |
| 6,678,559 B1 | 1/2004 | Breyen et al. | |
| 6,699,265 B1 | 3/2004 | O'Phelan et al. | |
| 6,721,602 B2 | 4/2004 | Engmark et al. | |
| 6,799,072 B2 | 9/2004 | Ries et al. | |
| 6,881,516 B2 | 4/2005 | Aamodt et al. | |
| 6,885,887 B2 | 4/2005 | O'Phelan et al. | |
| 6,963,482 B2 | 11/2005 | Breyen et al. | |
| 6,985,351 B2 | 1/2006 | O'Phelan et al. | |
| 7,479,349 B2 | 1/2009 | O'Phelan et al. | |
| 2002/0161404 A1 | 10/2002 | Schmidt | |
| 2003/0072124 A1 | 4/2003 | O'Phelan et al. | |
| 2003/0165744 A1 | 9/2003 | Schubert et al. | |
| 2003/0204216 A1 | 10/2003 | Ries et al. | |
| 2004/0127952 A1 * | 7/2004 | O'Phelan et al. | 607/36 |
| 2004/0147960 A1 | 7/2004 | O'Phelan et al. | |
| 2004/0147961 A1 | 7/2004 | O'Phelan et al. | |
| 2004/0174658 A1 | 9/2004 | O'Phelan et al. | |
| 2004/0220627 A1 * | 11/2004 | Crespi et al. | 607/5 |
| 2004/0230250 A1 | 11/2004 | Neumann et al. | |
| 2005/0041366 A1 | 2/2005 | Breven et al. | |
| 2005/0052825 A1 | 3/2005 | O'Phelan | |
| 2005/0154423 A1 * | 7/2005 | Goedeke et al. | 607/36 |
| 2005/0221171 A1 | 10/2005 | Haasl et al. | |
| 2005/0264979 A1 | 12/2005 | Breyen et al. | |
| 2006/0012942 A1 | 1/2006 | Poplett | |
| 2006/0023400 A1 | 2/2006 | Sherwood | |
| 2006/0247715 A1 | 11/2006 | Youker | |
| 2008/0091246 A1 | 4/2008 | Carey et al. | |
| 2010/0203380 A1 | 8/2010 | O'Phelan et al. | |

FOREIGN PATENT DOCUMENTS

| | | |
|---|---|---|
| WO | WO-2008/027639 A2 | 3/2008 |
| WO | WO-2008027639 A2 | 3/2008 |

OTHER PUBLICATIONS

"U.S. Appl. No. 09/165,779, Amendment and Response filed Apr. 18, 2001 to Office Action mailed Jan. 18, 2001", 17 pages.

"U.S. Appl. No. 09/165,779, Amendment and Response filed Aug. 4, 2000 to Non-Final Office Action mailed Apr. 5, 2000", 7 pages.

"U.S. Appl. No. 09/165,779, Non-Final Office Action Jan. 18, 2001", 6 pages.

"U.S. Appl. No. 09/165,779, Non-Final Office Action mailed Apr. 5, 2000", 7 pgs.

"U.S. Appl. No. 09/165,779, Non-Final Office Action mailed Jul. 30, 2002", 6 pgs.

"U.S. Appl. No. 09/165,779, Notice of Allowance mailed Nov. 7, 2002", 5 pgs

"U.S. Appl. No. 09/165,779, Notice of Allowance mailed Jul. 5, 2001", 5 pgs.

"U.S. Appl. No. 09/165,779, Notice of Allowance mailed Sep. 6, 2000", 5 pgs.

"U.S. Appl. No. 09/165,779, Response filed Aug. 30, 2002 to Non-Final Office Action mailed Jul. 30, 2002", 5 pgs.

"U.S. Appl. No. 09/165,779, Restriction Requirement mailed Jan. 19, 2000", 4 pgs.

"U.S. Appl. No. 10/360,551, Advisory Action mailed Jul. 7, 2006", 3 pgs.

"U.S. Appl. No. 10/360,551, Amendment and Response filed Apr. 6, 2006 to Office Action mailed Jan. 6, 2006", 7 pgs.

"U.S. Appl. No. 10/360,551, Amendment filed Jun. 14, 2006 to Final Office Action mailed Apr. 14, 2006", 8 pgs.

"U.S. Appl. No. 10/360,551, Appeal Brief filed Feb. 14, 2007", 17 pgs.

"U.S. Appl. No. 10/360,551, Examiner's Answer mailed May 10, 2007", 10 pgs.

"U.S. Appl. No. 10/360,551, Final Office Action mailed Apr. 14, 2006", 8 pgs.

"U.S. Appl. No. 10/360,551, Non-Final Office Action mailed Jan. 6, 2006", 6 pgs.

"U.S. Appl. No. 10/360,551, Pre-Appeal Brief Request for Review filed Sep. 14, 2006", 5 pgs.

"U.S. Appl. No. 10/360,551, Reply Brief filed Jul. 10, 2007", 4 pgs.

"U.S. Appl. No. 10/360,551, Response filed Nov. 14, 2005 to Restriction Requirement mailed Oct. 14, 2005", 5 pgs.

"U.S. Appl. No. 10/360,551, Restriction Requirement mailed Oct. 14, 2005", 12 pgs.

"U.S. Appl. No. 10/360,551, Notice of Allowance mailed Sep. 11, 2008", 6 pgs.

"U.S. Appl. No. 10/360,551, Decision on Appeal mailed Aug. 28, 2008", 7 pgs.

"U.S. Appl. No. 11/117,952, Non-Final Office Action Mailed Sep. 25, 2007", 8 pgs.

"U.S. Appl. No. 11/117,952, Response filed Dec. 26, 2007 to Non-Final Office Action mailed Sep. 25, 2007", 9 pgs.

"U.S. Appl. No. 11/117,952, Response filed Aug. 24, 2007 to Restriction Requirement mailed Jul. 24, 2007", 7 pgs.

"U.S. Appl. No. 11/117,952, Restriction Requirement mailed Jul. 24, 2007", 6 pgs.

"U.S. Appl. No. 11/117,952, Final Office Action mailed Apr. 24, 2008", 10 pgs.

"U.S. Appl. No. 11/467,808, Restriction Requirement mailed Feb. 5, 2009", 7 pgs.

"U.S. Appl. No. 11/467,808, Non-Final Office Action mailed Apr. 8, 2009", 9 pgs.

"U.S. Appl. No. 12/355,242, Non Final Office Action mailed Apr. 30, 2009", 8 pgs.

"International Application No. PCT/US2007/070697, International Search Report mailed Mar. 4, 2008", 4 pgs.

"International Application No. PCT/US2007/070697, Written Opinion mailed Mar. 4, 2008", 8 pgs.

"International Application No. PCT/US 03/41704, Invitation to Pay Additional fees and Partial International Search mailed Jun. 10, 2005", 16 pgs.

Fishbane, et al., "Physics for Scientists and Engineers,", *Prentice-Hall, Inc., vol II,*, (1993,), 791-793.

Haasl, B. J, et al., "Insulative Member on Battery Cathode", U.S. Appl. No. 11/140,854, filed May 31, 2005, 30 pgs.

Kelley, S., et al., "Method and Apparatus for Porous Insulative Film for Insulating Energy Source Layer", U.S. Appl. No. 11/127,025, filed May 11, 2005, 21 pgs.

Lunsman, P., et al., "High Energy Density Capacitors for Implantable Defibrillators", *Proceedings of the 16th Capacitor and Resistor Technology Symposium*, Monteleone Hotel, New Orleans, Louisiana, (Mar. 11-15, 1996), pp. 277-280.

O'Phelan, M. J., "Batteries Including A Flat Plate Design", U.S. Appl. No. 60/437,537, filed Dec. 31, 2002, 116 pgs.

Schmidt, B. L., et al., "Configurations and Methods for Making Capacitor Connections", U.S. Appl. No. 09/706,576, filed Nov. 3, 2000, 26 pgs.

Sherwood, G. J., "Method and Apparatus for High Voltage Aluminum Capacitor Design", U.S. Appl. No. 60/588,905, filed Jul. 16, 2004, 241 pgs.

Youker, N. A., "Method and Apparatus for an Implantable Pulse Generator With A Stacked Battery and Capacitor", U.S. Appl. No. 11/117,952, filed Apr. 29, 2005, 21 pgs.

"U.S. Appl. No. 11/467,808, Response filed Aug. 6, 2009 to Non Final Office Action mailed Apr. 8, 2009", 14 pgs.

"U.S. Appl. No. 11/467,808, Response filed Mar. 5, 2009 to Restriction Requirement mailed Feb. 5, 2009", 9 pgs.

"U.S. Appl. No. 12/355,242, Response filed Jul. 29, 2009 to Non Final Office Action mailed Apr. 30, 2009", 11 pgs.

"U.S. Appl. No. 11/467,808, Non-Final Office Action mailed Dec. 9, 2009", 8 pgs.

"U.S. Appl. No. 12/355,242, Final Office Action mailed Oct. 22, 2009", 11 pgs.

"U.S. Appl. No. 12/355,242, Response filed Dec. 10, 2009 to Final Office Action mailed Oct. 22, 2009", 8 pgs.

"U.S. Appl. No. 11/467,808, Final Office Action mailed Jul. 12, 2010", 10 pgs.

"U.S. Appl. No. 12/764,457, Restriction Requirement mailed Jul. 16, 2010", 7 pgs.

"U.S. Appl. No. 12/764,457, Response filed Sep. 16, 2010 to Restriction Requirement mailed Jul. 16, 2010", 6 pgs.

* cited by examiner

METHOD AND APPARATUS FOR AN IMPLANTABLE PULSE GENERATOR WITH A STACKED BATTERY AND CAPACITOR

CROSS REFERENCE TO RELATED APPLICATIONS

This application is a continuation of U.S. application Ser. No. 11/117,952, filed Apr. 29, 2005, now abandoned, the specification of which is herein incorporated by reference.

The following commonly assigned U.S. patents are related to the present application and are incorporated herein by reference in their entirety: "High-Energy Capacitors for Implantable Defibrillators," U.S. Pat. No. 6,556,863, filed Oct. 2, 1998, issued Apr. 29, 2003; "Flat Capacitor for an Implantable Medical Device," U.S. Pat. No. 6,699,265, filed Nov. 3, 2000, issued Mar. 2, 2004. Additionally, the present application is related to the following commonly assigned U.S. Patent Publication which is incorporated herein by reference in its entirety: "Method and Apparatus for Single High Voltage Aluminum Capacitor Design," Ser. No. 60/588,905, filed on Jul. 16, 2004. Further, the present application is related to the following commonly assigned U.S. Patent Application which is incorporated by reference in its entirety: "Batteries Including a Flat Plate Design," U.S. patent application Ser. No. 10/360,551 filed Feb. 7, 2003, which claims the benefit under 35 U.S.C 119(e) of U.S. Provisional Application Ser. No. 60/437,537 filed Dec. 31, 2002.

TECHNICAL FIELD

This disclosure relates generally to batteries and capacitors, and more particularly, to method and apparatus for an implantable pulse generator with a stacked battery and capacitor.

BACKGROUND

There is an ever-increasing interest in making electronic devices physically smaller. Consequently, electrical components become more compact as technologies are improved. However, such advances in technology also bring about additional problems. One such problem involves efficient packaging of components.

Components such as batteries, capacitors, and various additional electronics are often packaged together in electrical devices. As such, there is a need in the art for improved packaging strategies. Improvement could be realized by an overall increase in the efficiency of component packaging in existing devices. But improved systems must be robust and adaptable to various manufacturing processes.

SUMMARY

The above-mentioned problems and others not expressly discussed herein are addressed by the present subject matter and will be understood by reading and studying this specification.

One embodiment of the present subject matter includes a method of stacking flat battery layers into a battery stack; positioning the battery stack in a battery case, the planar battery surface having a battery perimeter; stacking flat capacitor layers into a capacitor stack; positioning the capacitor stack in a capacitor case, the planar capacitor surface having a capacitor perimeter; disposing the flat battery case and the flat electrolytic capacitor case in stacked alignment in a housing for implantation such that the battery perimeter and the capacitor perimeter are substantially coextensive; and hermetically sealing the housing.

Additionally, one embodiment of the present subject matter includes a battery having a plurality of flat battery layers disposed in a battery case, the battery case having a planar battery surface which has a battery perimeter; and a capacitor including a plurality of flat capacitor layers disposed in a capacitor case, the capacitor case having a planar capacitor surface which has a capacitor perimeter, the capacitor stacked with the battery such that the planar battery surface and the planar capacitor surface are adjacent, with the capacitor perimeter and the battery perimeter substantially coextensive; and a hermetically sealed implantable housing having a first shell and a lid mated to the first shell at a first opening, the first opening sized for passage of the battery and the capacitor, wherein the battery and the capacitor are disposed in the hermetically sealed implantable housing.

One embodiment of the present subject matter includes an apparatus having a hermetically sealed implantable device housing having a lid mated to an opening; programmable pulse generation electronics disposed in the hermetically sealed implantable device housing, the programmable pulse generation electronics sized for passage through the opening; battery means for powering the programmable pulse generation electronics, the battery means sized for passage through the opening; and capacitor means electrically interconnected to the battery means, the capacitor means for powering the programmable pulse generation electronics and sized for passage through the opening.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various"

embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Implantable medical devices are now in wide use for treating a variety of diseases. Cardiac rhythm management devices, as well as other types of implantable medical devices, are powered by a battery and a capacitor contained within the housing of the device. The size and shape of a battery which supplies sufficient power to operate the device is one factor which affects how small and physiologically shaped the housing of the device can be made. This is true for the capacitor as well. The present disclosure relates to a battery and capacitor and method for their construction, each suitable for use in an electronic device. Various embodiments are adapted for use in an implantable medical device. Overall, the present subject matter affords designers more freedom in packaging electronic device components into a housing.

Figure 1A:
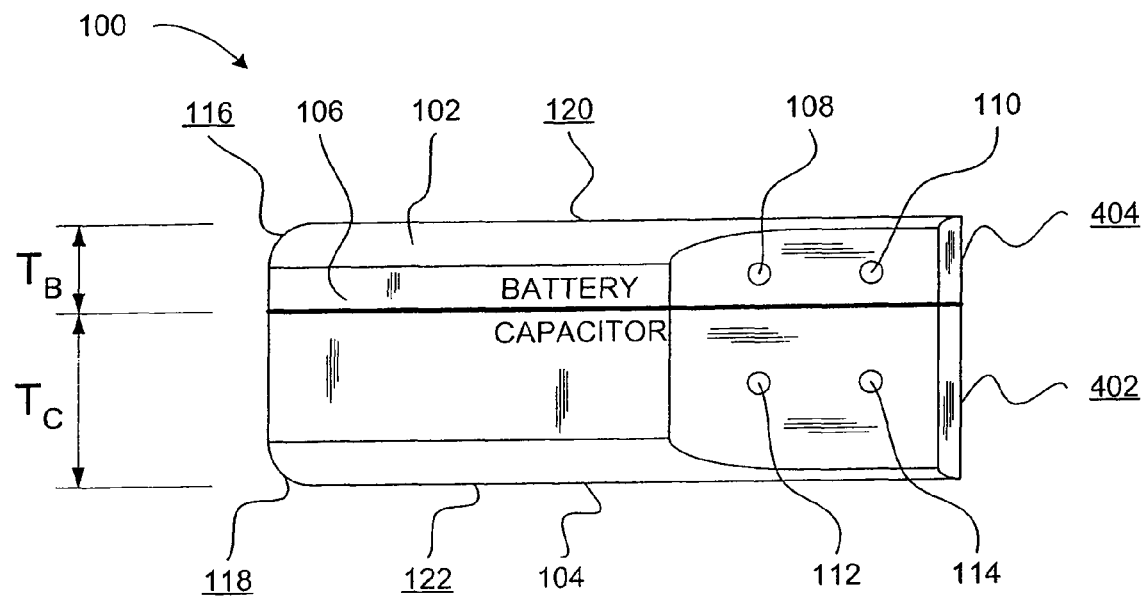
FIG. 1A is a side view of a power source, according to one embodiment of the present subject matter.

FIG. 1A is a side view of a power source 100, according to one embodiment of the present subject matter. In various embodiments, an example battery 102 includes a contour 116, which allows for positioning the battery 102 in various devices. For example, in various embodiments, battery 102 is shaped for placement in device adapted for chronic implantation. Additionally, in various embodiments, the battery 102 includes a feedthrough port 108, which is adapted for passage of one or more conductors. In various embodiments, the conductors at the feedthrough port 108 are connected to the battery anode. The battery additionally includes a feedthrough port 110 which, in various embodiments, is connected to the battery cathode. In some embodiments, a single feedthrough port is used instead of two feedthrough ports. Other embodiments include one or more feedthrough ports and a backfill port.

In various embodiments, the example capacitor 104 includes a contour 118, which allows for positioning the capacitor 104 in various devices. For example, in various embodiments, capacitor 104 is shaped for placement in a device adapted for chronic implantation. Additionally, in various embodiments, the capacitor 104 includes a feedthrough port 112, which is adapted for passage of one or more conductors. In various embodiments, the conductors at the feedthrough port 112 comprise a portion of the anode of the capacitor. The capacitor additionally includes a feedthrough port 114 which, in various embodiments, is connected to the battery cathode. In some embodiments, a single feedthrough port is used instead of two feedthrough ports. Other embodiments include one or more feedthrough ports and a backfill port.

In various embodiments, a device housing into which a battery and capacitor may be disposed has an interior. In some of these embodiments, the device interior has a first major interior face and a second major interior face. Battery and capacitor combinations can be shaped to mate to these faces. For example, in one embodiment, a battery face 120 is adapted for abutting an interior face of a housing. In some embodiments, the housing and the battery face 120 are separated from a housing by an insulator. The capacitor includes a face 122 which also is adapted for abutting an interior surface of a housing. Sidewall 402 and sidewall 404 are adapted for placement adjacent additional device components, in various embodiments.

Various embodiments maintain a continuous surface from sidewall 402 to sidewall 404. In various embodiments, the seam 106 defined by the adjacent battery 102 and capacitor 104 extends along a continuous surface. Thus, in various embodiments, the combined capacitor and battery are adapted for space efficient placement in a housing. In various embodiments, the housing is only marginally larger than the combined capacitor and battery so that the housing may accommodate those components. As such, various embodiments enable packaging additional devices in the housing adjacent the battery capacitor combination.

Battery 102 has a thickness $T_B$, in various embodiments. In various embodiments, the thickness is measured orthogonally, extending between interface 106 and surface 120. Additionally, capacitor 104 has a thickness $T_C$, in various embodiments. The thickness is measured orthogonally, extending between interface 106 and surface 122, in various embodiments. In various embodiments, the thicknesses $T_B$ and $T_C$ are selectable to fill the volume of a device housing. For example, in one embodiment, the present subject matter creates an index of a plurality of flat capacitors, the index created by measuring the thickness $T_C$ of each flat capacitor and storing that thickness in a first index. Additionally, in various embodiments, the present subject matter creates an index of a plurality of flat batteries, the index created by measuring the thickness $T_B$ of each flat battery and storing that thickness in a second index. The present subject matter than selects a battery and a capacitor having respective thicknesses $T_B$, $T_C$ selected to fill the volume of the targeted device housing.

Figure 1B:
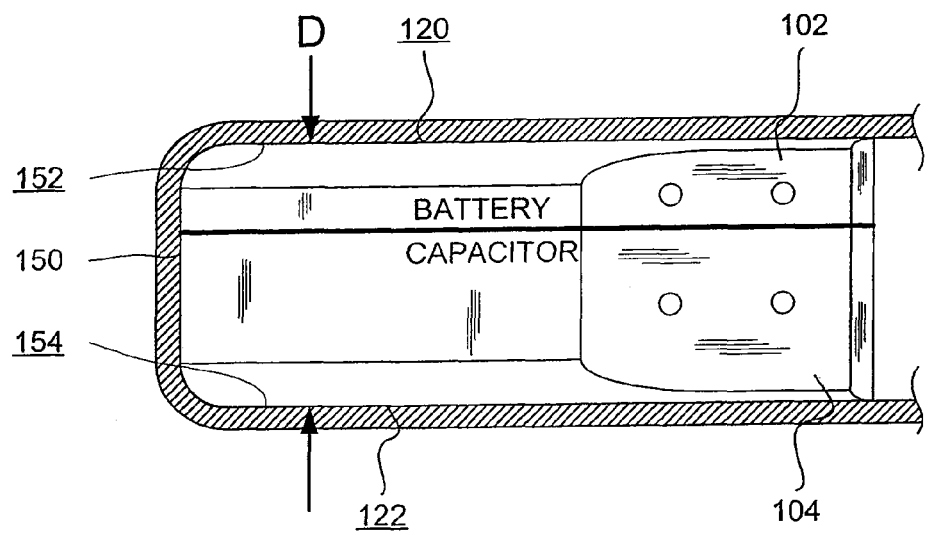
FIG. 1B illustrates a partial cross section of a device housing, a battery, and a capacitor, according to one embodiment of the present subject matter.

FIG. 1B illustrates a partial cross section of a device housing 150, a battery 102, and a capacitor 104, according to one embodiment of the present subject matter. In various embodiments, distance D extends between a first interior surface 152 for abutting a battery face 120, and a second interior surface 154 adapted for abutting surface 122. In various embodiments, the present subject matter selects a capacitor from a first index, and a battery from a second index, such that the combined thickness of the battery and the capacitor substantially match the thickness D. Additionally, in various embodiments, the selection of battery thickness and capacitor thickness is made in light of the thickness of adhesive layer and/or insulative layers disposed between the battery and the capacitor, and between these respective subcomponents and the device housing. In varying embodiments, the ratio between capacitor thickness and battery thickness is from about 7:1 to about 1.5:1. In additional embodiment, the ratio between the capacitor thickness and the battery thickness is from about 6:1 to about 2:1. Other ratios are possible without departing from the scope of the present subject matter.

In various embodiments, indexing of battery thickness, capacitor thickness, battery perimeter, capacitor perimeter, and other power source parameters is performed using a programmable computer. The present subject matter is not limited to indexes managed by programmable computers, however, as other indexing systems are within the scope of the present subject matter.

Figure 2:
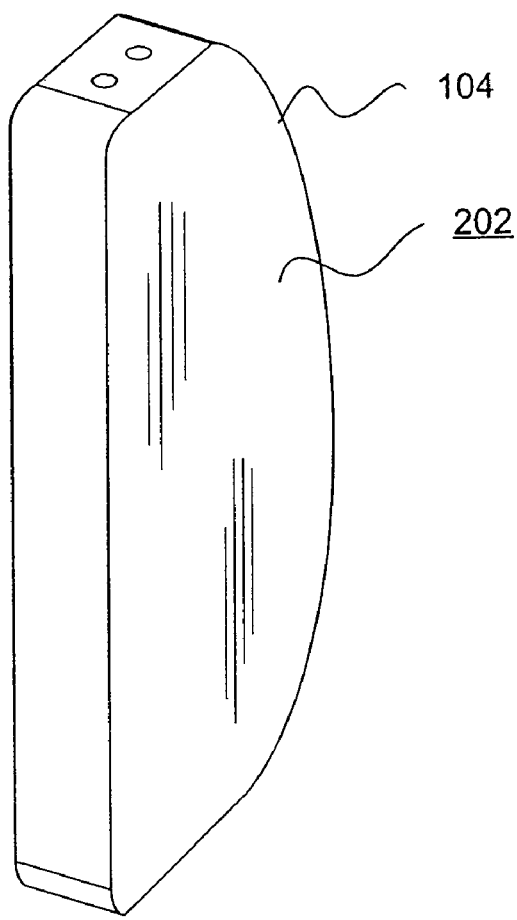
FIG. 2 is a perspective view of a capacitor, according to one embodiment of the present subject matter.

FIG. 2 is a perspective view of a capacitor, according to one embodiment of the present subject matter. Substantially flat electrolytic capacitors, in various examples, include a plurality of capacitor layers stacked together. In various embodiments, these stacks of capacitors are assembled into a capacitor case. Various cases are conductive or nonconductive. Some cases include feedthroughs through which conductors pass. The present subject matter includes, but is not limited to, embodiments disclosed on or around pages 12-37, 39, 41-140 of the following related and commonly assigned Provisional U.S. Patent Application "Method and Apparatus for Single High Voltage Aluminum Capacitor Design," Ser. No. 60/588, 905, filed on Jul. 16, 2004, incorporated herein by reference.

In various embodiments, the present subject matter includes a flat electrolytic capacitor 104 with a planar capacitor surface 202. In various embodiments, the planar capacitor surface includes a capacitor perimeter. In various embodiments, the capacitor stack is adapted to deliver between 7.0 Joules/cubic centimeter and 8.5 Joules/cubic centimeter. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

However, in some embodiments, the stack is disposed in a case, and linked with other components, a state which affects energy density in some embodiments. For example, in one packaged embodiment, including a case and terminals, the energy density available ranges from about 5.3 Joules per cubic centimeter of capacitor stack volume to about 6.3 Joules per cubic centimeter of capacitor stack volume. Some embodiments are adapted to deliver about 5.8 Joules. In various embodiments, these ranges are available at a voltage of between about 410 volts to about 610 volts.

Although these ranges embody one example possible within the scope of the subject matter, the subject matter is not so limited, and other capacitors without departing from the scope of the present subject matter.

Figure 3:
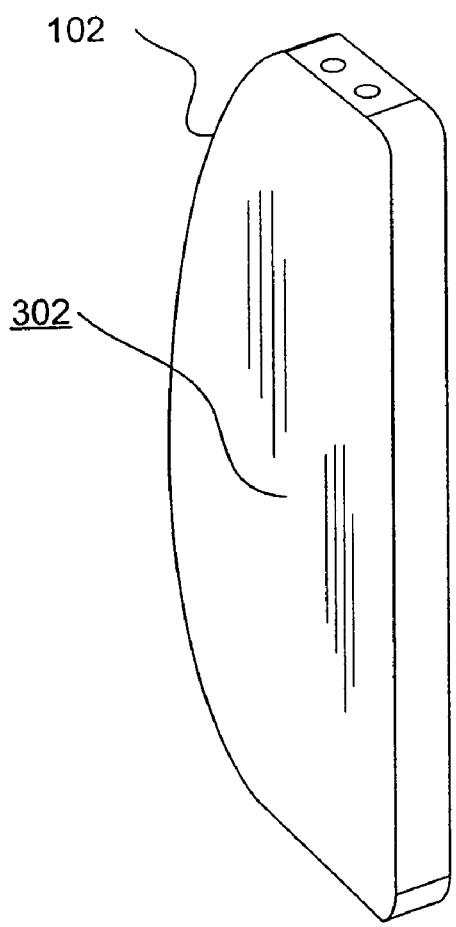
FIG. 3 is a perspective view of a battery, according to one embodiment of the present subject matter.

FIG. 3 is a perspective view of a battery, according to one embodiment of the present subject matter. In various embodiments, the battery 102 of the present subject matter is substantially flat. Substantially flat batteries, in various examples, include a plurality of battery electrodes stacked together, and further assembled into a battery case. Various battery cases are conductive or nonconductive. Some battery cases include feedthroughs. In various embodiments, the battery cases include a planar battery surface 302. The present subject matter includes, but is not limited to, embodiments disclosed at paragraphs 0095-0110, 0136-0196, 0206-0258 of the following related and commonly assigned U.S. patent application, "Batteries Including a Flat Plate Design," U.S. patent application Ser. No. 10/360,551, filed on Feb. 7, 2003, incorporated herein by reference.

Figure 4:
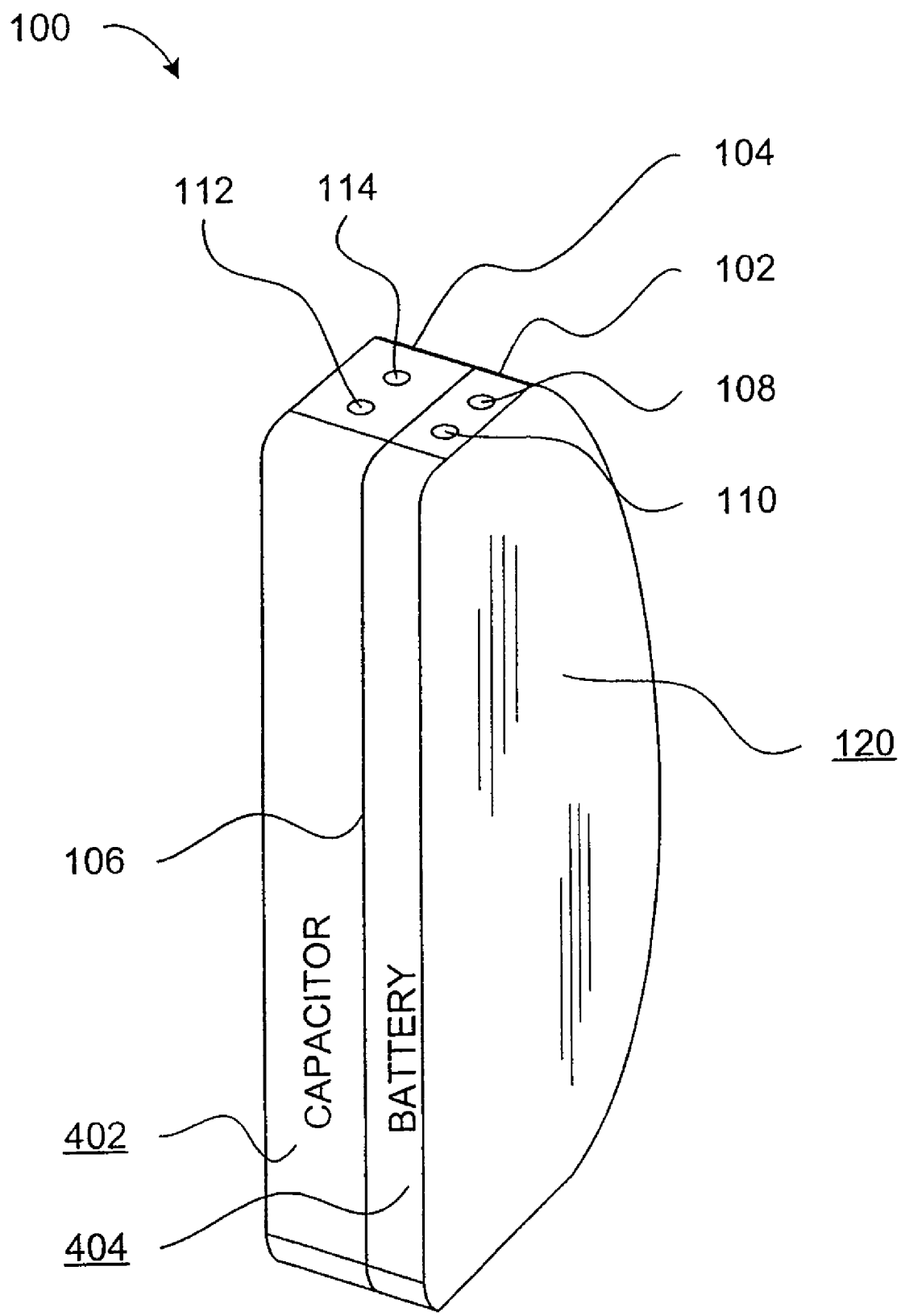
FIG. 4 is a perspective view of a battery and a capacitor, according to one embodiment of the present subject matter.

FIG. 4 is a perspective view of a battery and a capacitor, according to one embodiment of the present subject matter. In various embodiments, the present subject matter includes a power source 100 which has a battery 102 and a capacitor 104 mated at an interface 106, at which a planar battery surface and a planar capacitor surface are substantially coextensive. As a result of alignment, various embodiments demonstrate an overall envelope which is substantially continuous. Additionally, in various embodiments, the battery 102 includes a feedthrough ports 108, 110. Capacitor 104 includes feedthrough ports 112, 114, in various embodiments.

Various capacitor embodiments include a capacitor sidewall 402, and various battery embodiments include a battery sidewall 404. Various embodiments additionally include a battery face 120. A capacitor face is not visible in the illustration due to the orientation of the figure. In various examples, each of these respective case features is planar. When placed adjacent to one another, various embodiments include features which form a substantially planar overall sidewall which is the sum of each of the individual surfaces. In various embodiments, the overall surface is continuous. For example, sidewalls 402, 404 form a continuous surface. A continuous surface may have a linear shape, or a curvilinear shape. Embodiments having a continuous overall sidewall are within the scope of the present subject matter, however, additional embodiments are possible without departing from the scope of the scope of the present subject matter.

Figure 5:
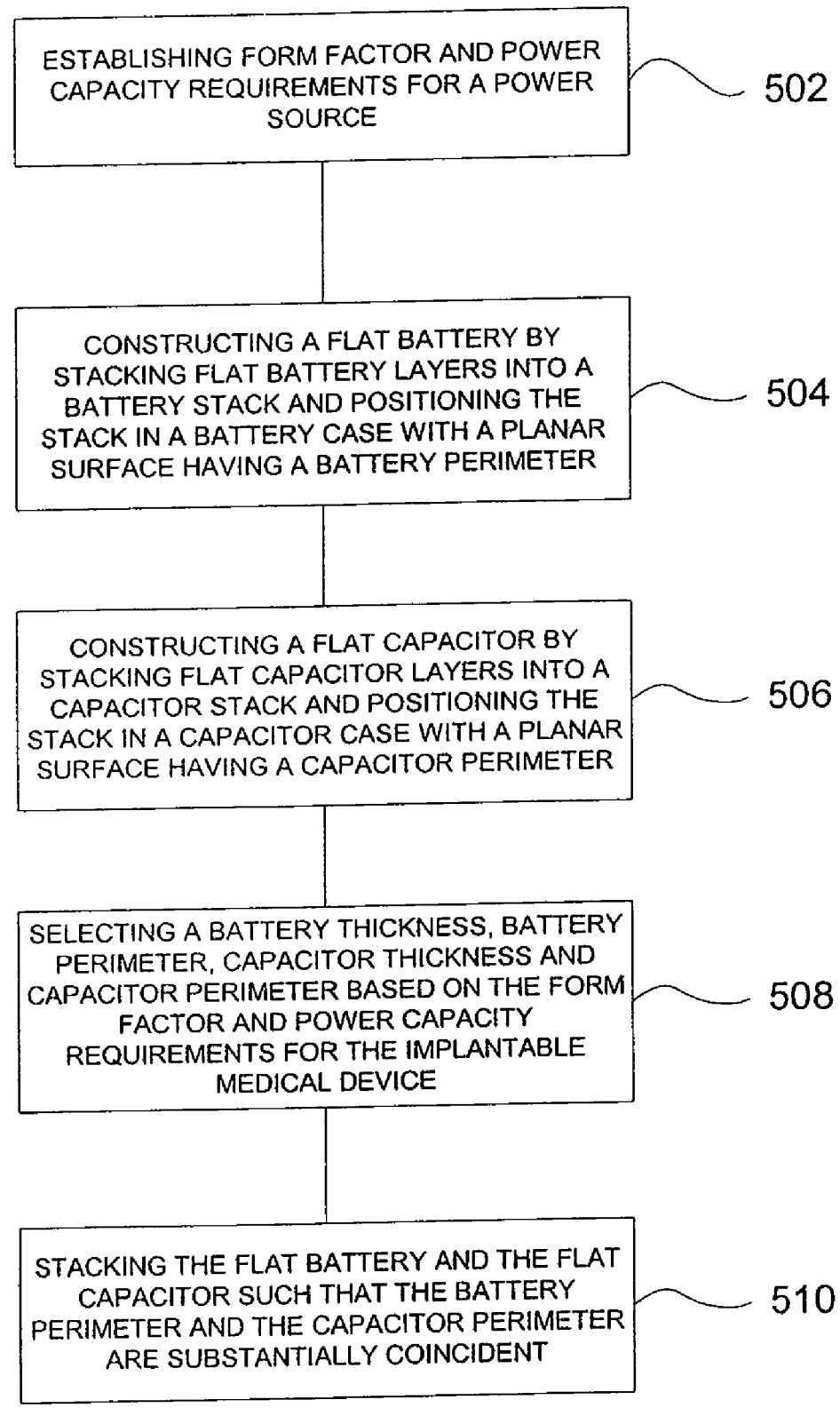
FIG. 5 is a method for constructing a battery and capacitor power source, according to one embodiment of the present subject matter.

FIG. 5 is a method for constructing a battery and capacitor power source, according to one embodiment of the present subject matter. In one embodiment of the present subject matter, the process includes establishing form factor and power capacity requirements for a power source to be used in an implantable medical device 502. The embodiment includes constructing a flat battery by stacking flat battery layers into a battery stack and positioning the stack in a battery case with a planar interface and a battery perimeter and battery thickness 504. The embodiment further includes constructing a flat electrolytic capacitor by stacking flat capacitor layers into a capacitor stack and positioning the stack in a capacitor case with a planar interface and a capacitor perimeter and capacitor thickness 506. The embodiment additionally includes stacking the flat battery and the flat electrolytic capacitor such that the battery perimeter and the capacitor perimeter are substantially coextensive 510. This embodiment is illustrative of the present subject matter, but it should be noted that other combinations of steps, and additional steps, also lie within the scope of the present subject matter.

For example, in some embodiments, a battery thickness, battery perimeter, capacitor thickness and capacitor perimeter are selected based on form factor and power capacity requirements for an implantable medical device 508. Additionally, various method embodiments include measuring a ratio between battery thickness and capacitor thickness, and using this ratio in selecting a battery and capacitor. A ratio is be established by known power requirements, in various embodiments. Another example combines size requirements with power requirements in selecting a ratio. The ratio can be stored and used by a design process or manufacturing process to discern the mechanical and electrical composition of a needed power source, in various embodiments.

In various embodiments, the present subject matter includes delivering from the flat battery and the flat electrolytic capacitor from about 1.25 Joules per Amp hour of battery capacity to about 50 Joules per amp hour of battery capacity. In some of these embodiments, the flat battery has a battery capacity density of from about 0.23 amp hours per cubic centimeter of flat battery to about 0.25 amp hours per cubic centimeter of flat battery. Battery capacity density is measured by dividing the amp-hour rating of the battery by the battery volume, in various embodiments. The present subject matter includes, but is not limited to, embodiments disclosed at paragraphs 0095-0110, 0136-0196, 0206-0258 of the following related and commonly assigned U.S. Patent Publication, "Batteries Including a Flat Plate Design," U.S. Patent Publication No. 2004/0127952, filed on Feb. 7, 2003, incorporated herein by reference.

In additional embodiments, the flat electrolytic capacitor includes an energy density of from about 4.65 joules per cubic centimeter of flat electrolytic capacitor to 6.5 joules per cubic centimeter of flat electrolytic capacitor. The present subject matter includes, but is not limited to, embodiments disclosed on or around pages 12-37, 39, 41-140 of the following related and commonly assigned Provisional U.S. Patent Application "Method and Apparatus for Single High Voltage Aluminum Capacitor Design," Ser. No. 60/588,905, filed on Jul. 16, 2004, incorporated herein by reference.

Various methods of the present subject matter benefit from selecting capacitor stack layers and battery stack layers which are substantially parallel to their coextensive case interfaces. By constructing the power source as such, various benefits are possible. For example, in one embodiment, a single two-axis machine can position capacitor layers in a stack, position the capacitor stack in a capacitor case, position battery layers in a stack, and position the battery stack in a battery case. In one embodiment, the single two-axis machine is a pick-and-place machine. This combination is provided for illustration, but other combinations of these steps are possible, and additional steps are also within the scope of the present subject matter.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and various embodiments, will be apparent to those of skill in the art upon reviewing the above description. The scope of the present subject matter should be determined with reference to the appended claims, along with the full scope of equivalents to which such claims are entitled.

I claim:

1. A method for constructing a configurable power source for an implantable device, comprising:
   providing a housing for a battery and a capacitor, the housing having a distance D between a first internal face and a second internal face, the housing adapted to fit within dimensions of the implantable device;
   providing a plurality of batteries of different thicknesses, each battery disposed in a respective battery case adapted to fit within a perimeter of the housing and each battery comprising a plurality of planar anode and cathode layers wherein each layer is separated by a battery separator layer;
   providing plurality of capacitors of different thicknesses, each capacitor disposed in a respective capacitor case adapted to fit within the housing and adjacent the battery and each capacitor comprising a unitary electrolyte, and a plurality of planar anode and cathode layers separated by a plurality of planar capacitor separator layers; and
   forming the configurable power source comprising:
      selecting the battery from the plurality of batteries, the battery having a battery thickness;
      selecting the capacitor from the plurality of capacitors by referencing the battery thickness and an index of respective thicknesses of the plurality of capacitors to select a capacitor such that a combined thickness of the selected battery and the selected capacitor is about equal to the distance D; and
   placing the battery and the capacitor in the housing.

2. The method of claim 1, wherein the voltage of operation of the selected battery and the selected capacitor is between about 410 volts and 610 volts.

3. The method of claim 1, wherein selecting the battery from the plurality of batteries includes selecting a battery having a battery energy density from about 0.23 amp hours per cubic centimeter to about 0.25 amp hours per cubic centimeter.

4. The method of claim 1, wherein selecting the capacitor from the plurality of capacitors includes selecting a capacitor having a capacitor energy density from about 7.0 joules per cubic centimeter to about 8.5 joules per cubic centimeter.

5. The method of claim 4, wherein selecting the battery from the plurality of batteries includes selecting a battery having a battery energy density from about 0.23 amp hours per cubic centimeter to about 0.25 amp hours per cubic centimeter.

6. The method of claim 1, wherein selecting the capacitor from the plurality of capacitors includes selecting a capacitor having a capacitor energy density from about 5.3 joules per cubic centimeter to about 6.3 joules per cubic centimeter.

7. The method of claim 6, wherein selecting the battery from the plurality of batteries includes selecting a battery having a battery energy density from about 0.23 amp hours per cubic centimeter to about 0.25 amp hours per cubic centimeter.

8. The method of claim 1, wherein selecting a battery includes selecting a battery from the plurality of batteries using a pick and place device.

9. The method of claim 1, wherein selecting a capacitor includes selecting a capacitor from the plurality of capacitors using a pick and place device.

10. The method of claim 1, wherein forming the configurable power source further comprising:
    inserting the battery into the housing;
    inserting the capacitor adjacent the battery into the housing;
    connecting one or more battery feedthrough ports;
    connecting one or more capacitor feedthrough ports; and
    sealing the housing.

11. The method of claim 1, wherein selecting a capacitor includes selecting a capacitor from the plurality of capacitors to at least meet a predetermined power density requirement of the implantable device.

12. The method of claim 1, wherein selecting a battery includes selecting a battery from the plurality of batteries to at least meet a predetermined power density requirement of the implantable device.

13. The method of claim 1, wherein selecting a capacitor and selecting a battery includes selecting a battery and capacitor combination from the pluralities of batteries and the plurality of capacitors such that the battery and capacitor combination at least meet a predetermined power density requirement of the implantable device.

* * * * *